(12) United States Patent
van Muijen et al.

(10) Patent No.: US 6,677,118 B1
(45) Date of Patent: Jan. 13, 2004

(54) PROCESS FOR THE DETERMINATION OF CTP11 AND FOR DETERMINING WHETHER A TUMOR SAMPLE HAS METASTATIC POTENTIAL

(75) Inventors: Goos van Muijen, Nijmegen (NL); Albert Zendman, Beuningen (NL)

(73) Assignee: Hoffman-La Roche Inc., Nutley, NJ (US)

( * ) Notice: Subject to any disclaimer, the term of this patent is extended or adjusted under 35 U.S.C. 154(b) by 552 days.

(21) Appl. No.: 09/709,902

(22) Filed: Nov. 10, 2000

(30) Foreign Application Priority Data

Nov. 11, 1999 (EP) .............................. 99122454

(51) Int. Cl.⁷ .......................... C12Q 1/63; C07H 21/04
(52) U.S. Cl. .......................... 435/6; 435/7.1; 536/23.1; 536/24.3; 536/24.31; 536/24.5
(58) Field of Search ................ 435/6, 7.1; 536/23.1, 536/24.3, 24.31, 24.5

(56) References Cited

FOREIGN PATENT DOCUMENTS

| EP | 19811193 | 9/1999 |
|----|----------|--------|
| WO | WO 97/36535 | 10/1997 |

OTHER PUBLICATIONS

EMBL Database—XP002145787—Aug. 23, 1999.
EMBL Database—XP002145788—May 5, 1997.
EMBL Database—XP002145789—May 5, 1997.
Bao et al., Clinical & Experimental Metastasis, vol. 16, No. 3, 4/98 pp. 227–233.
Chen et al., Proc. Natl. Acad. Sci. USA vol. 94, pp. 1914–1918, 3/97.
Zendman et al., Cancer Research vol. 59 pp. 6223–6229, Dec. 15, 1999.
Chen, Y. et al., Proc. Natl. Acad. Sci. USA, vol. 95, pp. 6919–6923, 6/98.
Van Der Bruggen, P. et al., Science, vol. 254 pp. 1643–1647 (1991).
Westbrook, V. et al., Biology of Reproduction, vol. 63, pp. 469–481, Feb. 4, 2000.
Abstract corresponding to DE 19811193.

*Primary Examiner*—David Guzo
*Assistant Examiner*—Ramin Akhavan
(74) *Attorney, Agent, or Firm*—George W. Johnston; Patricia S. Rocha-Tramaloni

(57) ABSTRACT

A process for the determination of CTp11 and for determining whether a tumor sample has metastatic potential is provided.

6 Claims, 3 Drawing Sheets

```
                                                    ━━━━━━━━━━━━━━━━━━━▶
caaaagcctgccgcagacattgaagaaccaatatataca ATG GAC AAA CAA TCC  54
                                         M   D   K   Q   S    5
                                         ─────────────────

AGT GCC GGC GGG GTG AAG AGG AGC GTC CCC TGT GAA TCC AAC GAG  99
 S   A   G   G   V   K   R   S   V   P   C   E   S   N   E   20
━━▶
GTG AAT GAG ACG ATG CCG GAG ACC CCA ACT GGG GAC TCA GAC CCG 144
 V   N   E   T   M   P   E   T   P   T   G   D   S   D   P   35

CAA CCT GCT CCT AAA AAA ATG AAA ACA TCT GAG TCC TCG ACC ATA 189
 Q   P   A   P  ┌K   K   M   K   T   S   E   S   S   T   I┐  50

CTA GTG GTT CGC TAC AGG AGG AAC GTG AAA AGA ACA TCT CCA GAG 234
 L   V   V   R   Y   R   R│ N   V   K   R   T   S   P   E   65
                                ◀━━━━━━━━━━━━━━━━━━━
GAA CTG CTG AAT GAC CAC GCC CGA GAG AAC AGA ATC AAC CCC CTC 279
 E   L   L   N   D   H   A   R   E   N   R   I   N   P   L   80
        ◀━━━━━━━━━━━━━
CAA ATG GAG GAG GAG GAA TTC ATG GAA ATA ATG GTT GAA ATA CCT 324
 Q   M   E   E   E   E   F   M   E   I   M   V   E   I   P   95
        ═══════════════════════════

GCA AAG TAG caagaagctacatctctcaaccttgggcaatgaaaataaagtttgag 380
 A   K   *                                    ─────────      97 aagctgaaaaaaaaaaaaaaaaaaaa                                  408
```

PROCESS FOR THE DETERMINATION OF CTP11 AND FOR DETERMINING WHETHER A TUMOR SAMPLE HAS METASTATIC POTENTIAL

FIELD OF THE INVENTION

The present invention provides methods in the field of cancer diagnosis. In particular, A process for the determination of CTp11 (cancer/testis-associated protein of 11kDl) and for determining whether a tumor sample has metastatic potential is provided.

BACKGROUND OF THE INVENTION

In order for metastasis of cancer to occur, several hurdles must be overcome, such as degradation of the extracellular matrix and basal membrane, intra- and extravasation of vessels of the blood and of the lymphatic system, escape by the attack of the immune system, and homing and colonization of distant organs (Pardee, A. B., Advances in Cancer Res. 65 (1994) 213–227; Ponta, H., et al., Biochem. Biophys. Acta 1198 (1994) 1–10). A further level of complexity is achieved in that different types of cancers make use of different molecular mechanisms for metastasis and exhibit different tropism of metastasis.

Metastasizing and non-metastasizing human melanoma cell lines have been important tools in identifying differentially expressed genes and for investigation of their role in metastasis (Weterman, M. A. J., et al., Cancer Res. 52 (1992) 1291–1296; Weterman, M. A. J., et al., Int. J. Cancer 53 (1993) 278–284; Van Groningen, J. M., et al., Cancer Res. 55 (1995) 6237–6243; Weterman, M. A. J., et al., Int. J. Cancer 60 (1995) 73–81; van Muijen, G. N. P., et al., Int. J. Cancer 48 (1991) 85–91; van Muijen, G. N. P., et al., Clin. Ekp. Metastasis 9 (1991) 259–272).

Cell adhesion molecules play an important role in the invasion, dissemination, extravasation and lodging of tumor cells. The interaction of disseminated tumor cells with endothelium and tissue stroma is supposed to be one of the critical steps in tumor progression and metastasis formation (Ebnet, K., et al., Annu. Rev. Immunol. 14 (1996) 155–177; Varner, J. A., and Cheresh, D. A., Curr. Opin. Cell Biol. 8 (1996) 724–730; Albelda, S. M., Lab. Invest. 68 (1993) 4–17).

CTp11 is a polypeptide homologous to the polypeptide sequences described in EMBL Database AI962751, AA412605, and AA412270 as well as in SEQ ID NO:18 and SEQ ID NO:75 of WO 99/46374.

SUMMARY OF THE INVENTION

In accordance with the present invention, it was surprisingly found that a protein, termed CTp11 (cancer/testis-associated protein of 11 kD), is upregulated in metastatic cancer cells as compared to their non-metastatic counterparts. CTp11 may be involved in promotion of several steps of the metastatic cascade. CTp11 is a specific marker of metastatic cancer cells, due to the fact that it can be presented in an MHC Class I complex on cytotoxic T cells but is not presented naturally because the only non-tumor cells (testis cells) in which CTp11 is found do not present antigens in an MHC Class I context. The CTp11 gene codes for a polypeptide of SEQ ID NO:2.

The present invention provides a process for detecting the presence or absence of at least one specific nucleic acid or mixture of nucleic acids, or distinguishing between two different sequences in said sample, wherein the sample is suspected of containing said sequence or sequences, which process comprises the following steps in order:

(a) incubating said sample under stringent hybridization conditions with a nucleic acid probe which is selected from the group consisting of:
  (i) a nucleic acid sequence of SEQ ID NOS: 1 and 3 to 6;
  (ii) a nucleic acid sequence which is exactly complementary to a nucleic acid sequence of (i);
  (iii) a nucleic acid sequence which hybridizes under stringent conditions with the sequence of (i); and
  (iv) a nucleic acid sequence which hybridizes under stringent conditions with the sequence of (ii); and
(b) determining whether said hybridization has occurred.

Moreover, the present invention provides a process for determining whether or not a cancer cell-containing test sample has potential for tumor progression or metastasis, wherein the test sample and a cancer cell-containing sample which is free from metastasis and wherein both samples are obtained from the same individual or different individuals of the same species, which process comprises the following steps:

(a) incubating each respective sample under stringent hybridization conditions with a nucleic acid probe which is selected from the group consisting of:
  (i) a nucleic acid sequence of SEQ ID NOS: 1 and 3 to 6;
  (ii) a nucleic acid sequence which is exactly complementary to a nucleic acid sequence of (i);
  (iii) a nucleic acid sequence which hybridizes under stringent conditions with the sequence of (i); and
  (iv) a nucleic acid sequence which hybridizes under stringent conditions with the sequence of (ii); and
(b) determining the approximate amount of hybridization of each respective sample with said probe, and
(c) comparing the approximate amount of hybridization of the test sample to an approximate amount of hybridization of the sample which is free from metastasis, to identify whether or not the test sample contains a greater amount of the specific nucleic acid or mixture of nucleic acids than does the sample which is free from metastasis.

DESCRIPTION OF THE FIGURES

FIG. 2 CTp11 cDNA and deduced protein sequence. Primers used for PCR are indicated by arrows (first PCR: closed arrowheads; nested PCR: open arrowheads). Polyadenylation signal is underlined, putative nuclear localization signal is boxed and poly-E acidic domain is double underlined. The stop codon is marked by an asterisk.

DETAILED DESCRIPTION OF THE INVENTION

The present invention provides methods of use and the use of CTp11 gene (cancer/testis-associated protein of 11 kD) for diagnostics, especially in the field of cancer diagnosis. In particular, the invention involves the identification of said gene CTp11 in malignant tumor cells having a metastatic and/or progression potential.

Figure 1:
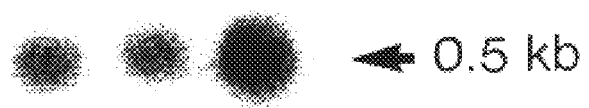
FIG. 1 Northern blot analysis on a panel of human melanoma cell lines with different metastatic capacity after subcutaneous inoculation into nude mice. The blot is hybridized with the 300 bp differential display cDNA. Arrow indicates a band of 0.5 kb exclusively present in the highly metastatic cell lines. Lane 1: 530; lane 2: 1F6; lane 3: M14; lane 4: Mel57; lane 5: MV3; lane 6: BLM; lane 7: 1F6m.

Differential Display Technique applied to non-metastatic melanoma cell line 1F6 and its metastatic subcell line 1F6m resulted in identification of CTp11 which was at least 40 fold up-regulated in the metastatic cell line (FIG. 1).

According to the invention, the nucleic acid molecule (CTp11) has upregulated expression in metastatic tumor cells and is capable of inducing tumor progression and/or metastasis, especially in malignant melanoma and mammary carcinoma cells. The nucleic acid (CTp11) has the sequence SEQ ID NO:1 or it is a nucleic acid which, because of the degeneracy of the genetic code, differs from SEQ ID NO:1, but which encodes the amino acid sequence encoded by the nucleic acid of SEQ ID NO: 1.

The isolated CTp11 polypeptide can occur in natural allelic variations which differ from individual to individual. Such variations of the amino acids are usually amino acid substitutions. However, they may also be deletions, insertions or additions of amino acids to the total sequence. The CTp11 protein according to the invention—depending, both in respect of the extent and type, on the cell and cell type in which it is expressed—can be in glycosylated or non-glycosylated form. Polypeptides with metastatic activity can be identified by transfection of CTp11-negative non-metastasizing tumor cells with expression vectors for CTp11, establishment of stable transfectants and evaluation of in vitro invasiveness in Matrigel invasion assays and their metastatic capacity after xenografting into nude mice.

"Polypeptide with CTp11 activity or CTp11" means also proteins with minor amino acid variations but with substantially the same CTp11 activity. Substantially the same means that the activities are of the same biological properties and the polypeptides show (at least 90%, preferably more than 95%) homology, or preferably identity, in amino acid sequence. Homology can be examined by using the BLAST algorithm described by Altschul, S. F., et al., Nucleic Acids Res. 25 (1997) 3389–3402.

The term "nucleic acid molecule or nucleic acid" denotes a polynucleotide molecule which can be, for example, a DNA, RNA, or derivatized active DNA or RNA. DNA and/or RNA molecules are preferred, however.

The term "hybridize under stringent conditions" means that two nucleic acid fragments are capable of hybridization to one another under standard hybridization conditions described in Sambrook et al., Molecular Cloning: A Laboratory Manual (1989) Cold Spring Harbor Laboratory Press, New York, USA. More specifically, "stringent conditions" as used herein refer to hybridization at 65° C. in a hybridization buffer consisting of 250 mmol/l sodium phosphate buffer pH 7.2, 7% (w/v) SDS, 1% (w/v) BSA, 1 mmol/l EDTA and 0.1 mg/ml single-stranded salmon sperm DNA. A final wash is performed at 65° C. in 125 mmol/l sodium phosphate buffer pH 7.2, 1 mmol/l EDTA and 1% (w/v) SDS.

The phrase "nucleic acid or polypeptide" as used throughout this application refers to a nucleic acid or polypeptide having a CTp11 activity which is substantially free of cellular material or culture medium when produced by recombinant DNA techniques, or substantially free of chemical precursors or other chemicals when synthesized chemically. Such a nucleic acid is preferably free of sequences which naturally flank the nucleic acid (i.e. sequences located at the 5' and the 3' ends of the nucleic acid) in the organism from which the nucleic acid is derived.

The CTp11 polypeptides can be produced by recombinant means in host cells, using an expression vector, or can be produced synthetically. Non-glycosylated CTp11 polypeptide is obtained when it is produced recombinantly in prokaryotes. With the aid of the nucleic acid sequences provided by the invention it is possible to search for the CTp11 gene or its variants in genomes of any desired cells (e.g. apart from human cells, also in cells of other mammals), to identify these and to isolate the desired gene coding for the CTp11 protein. Such processes and suitable hybridization conditions are known to a person skilled in the art and are described, for example, by Sambrook et al., Molecular Cloning: A Laboratory Manual (1989), Cold Spring Harbor Laboratory Press, New York, USA, and Hames, B. D., Higgins, S. G., Nucleic Acid Hybridisation—A Practical Approach (1985) IRL Press, Oxford, England. In this case the standard protocols described in these publications are usually used for the experiments.

With the aid of such nucleic acids, CTp11 protein can be obtained in a reproducible manner and in large amounts. For expression in prokaryotic or eukaryotic organisms, such as prokaryotic host cells or eukaryotic host cells, the nucleic acid is integrated into suitable expression vectors, according to methods familiar to a person skilled in the art. Such an expression vector preferably contains a regulatable/inducible promoter. These recombinant vectors are then introduced for the expression into suitable host cells such as, e.g., *E. coli* as a prokaryotic host cell or *Saccharomyces cerevisiae*, Teratocarcirioma cell line PA-1 sc 9117 (Büttner et al., Mol. Cell. Biol. 11 (1991) 3573–3583), insect cells, CHO or COS cells as eukaryotic host cells and the transformed or transduced host cells are cultured under conditions which allow expression of the heterologous gene. The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. Also in vitro reactivation of the protein may be necessary if it is not found in soluble form in the cell culture.

CTp11 can be purified after recombinant production by affinity chromatography using known protein purification techniques, including immunoprecipitation, gel filtration, ion exchange chromatography, chromatofocussing, isoelectric focussing, selective precipitation, electrophoresis, or the like.

The invention comprises a method for detecting a nucleic acid molecule of gene CTp11, comprising incubating a sample (e.g., body fluids such as blood, cell lysates) with a specifically binding nucleic acid molecule and determining hybridization under stringent conditions of said isolated nucleic acid molecule to a target nucleic acid molecule for determination of presence of a nucleic acid molecule which is the CTp11 gene and therefore a method for the identification of the metastatic potential and/or progression of tumor cells.

To determine whether a cancer cell-containing test sample has potential for tumor progression or metastasis, the approximate amount of hybridization of the isolated nucleic acid with the target nucleic acid or nucleic acids is determined. The approximate amount of hybridization need not be determined quantitatively, although a quantitative determination is encompassed by the present invention. Typically, the approximate amount of hybridization is determined qualitatively, for example, by a sight inspection upon detecting hybridization. For example, if a gel is used to resolve labelled nucleic acid which hybridizes to target nucleic acid in the sample, the resulting band can be inspected visually. When performing a hybridization of isolated nucleic acid in a cancer-containing sample which is free from metastasis from an individual of the same species, the same protocol is followed. One can compare the approximate amount of hybridization in the test sample to the approximate amount of hybridization in the sample free from metastasis, to identify whether or not the test sample contains a greater amount of the target nucleic acid or nucleic acids than does the sample which is free from metastasis. For visual inspection in particular, it is recommended that an appreciable difference by visualized to assess that the test sample contains a greater amount of the target nucleic acid or nucleic acids.

As is shown in accordance with the present invention, the CTp11 nucleic acid is present in a greater amount in a metastasized tumor sample than in a sample free from metastasis. A test sample having potential for tumor progression or metastasis will have a greater amount of the CTp11 nucleic acid than does a cancer cell sample which is free from metastasis. To identify a test sample as containing upregulated CTp11 nucleic acid, i.e., wherein the cancer cells have potential for tumor progression or metastasis, it is preferable that the test sample have an approximate amount of CTp11 nucleic acid which is appreciably greater that the approximate amount in a non-metastasigned sample. For example, a test sample having an upregulated CTp11 gene may have approximately 15- to approximately 60- fold greater amount of CTp11 gene than a non-metastasized sample.

On the basis of the nucleic acids provided by the invention it is possible to provide a test which can be used to detect nucleic acids with upregulated expression in metastatic human tumor cells. Such a test can be carried out by means of nucleic acid diagnostics. In this case the sample to be examined is contacted with a probe that is selected from the group comprising
 a) the nucleic acid sequence shown in SEQ ID NOS:1 and 3 to 6 or a nucleic acid sequence which is complementary to one of these nucleic acid sequences, and
 b) nucleic acids which hybridize under stringent conditions with one of the nucleic acids from a), wherein the nucleic acid probe is incubated with the nucleic acid of the sample and the hybridization is detected optionally by means of a further binding partner for the nucleic acid of the sample and/or the nucleic acid probe. For obtaining a nucleic acid by hybridization in accordance with b), it is preferable to hybridize to the probe shown in SEQ ID NOS:3 to 6 or a sequence complementary thereto. Hybridization between the probe used and nucleic acids from the sample indicates the presence of the RNA of such proteins.

Methods of hybridization of a probe and a nucleic acid are known to a person skilled in the art and are described, for example, in WO 89/06698, EP-A 0 200 362, U.S. Pat. No. 2,915,082, EP-A 0 063 879, EP-A 0 173 251, EP-A 0 128 018.

In a preferred embodiment of the invention the coding nucleic acid of the sample is amplified before the test, for example by means of the known PCR technique. Usually a derivatized (labeled) nucleic acid probe is used within the framework of nucleic acid diagnostics. This probe is contacted with a denatured DNA or RNA from the sample which is bound to a carrier and in this process the temperature, ionic strength, pH and other buffer conditions are selected—depending on the length and composition of the nucleic acid probe and the resulting melting temperature of the expected hybrid—such that the labeled DNA or RNA can bind to homologous DNA or RNA (hybridization see also Wahl, G. M., et al., Proc. Natl. Acad. Sci. USA 76 (1979) 3683–3687). Suitable carriers are membranes or carrier materials based on nitrocellulose (e.g., Schleicher and Schüll, BA 85, Amersham Hybond, C.), strengthened or bound nitrocellulose in powder form or nylon membranes derivatized with various functional groups (e.g., nitro groups) (e.g., Schleicher and Schüll, Nytran; NEN, Gene Screen; Amersham Hybond M.; Pall Biodyne).

Hybridizing DNA or RNA is then detected by incubating the carrier with an antibody or antibody fragment after thorough washing and saturation to prevent unspecific binding. The antibody or the antibody fragment is directed towards the substance incorporated during hybridization to the nucleic acid probe. The antibody is in turn labeled. However, it is also possible to use a directly labeled DNA. After incubation with the antibodies it is washed again in order to only detect specifically bound antibody conjugates. The determination is then carried out according to known methods by means of the label on the antibody or the antibody fragment.

The detection of the expression can be carried out for example as:
 in situ hybridization with fixed whole cells, with fixed tissue smears and isolated metaphase chromosomes,
 colony hybridization (cells) and plaque hybridization (phages and viruses),
 Southern hybridization (DNA detection),
 Northern hybridization (RNA detection),
 serum analysis (e.g., cell type analysis of cells in the serum by slot-blot analysis),
 after amplification (e.g., PCR technique).

Therefore the invention includes a method for the detection of the metastatic potential of melanoma and mammary carcinoma cells, comprising
 a) incubating a sample of body fluid of a patient suffering from cancer, of melanoma cancer cells, of mammary carcinoma cells, or of a cell extract or cell culture supernatants of said cancer cells, whereby said sample contains nucleic acids with a nucleic acid probe which is selected from the group consisting of
  (i) the nucleic acid shown in SEQ ID NOS:1 and 3 to 6 or a nucleic acid which is complementary to said nucleic acid sequence, and
  (ii) nucleic acids which hybridize with the nucleic acids from (i) and
 b) detecting hybridization by means of a further binding partner of the nucleic acid of the sample and/or the nucleic acid probe or by X-ray radiography.

Preferably the nucleic acid probe is incubated with the nucleic acid of the sample and the hybridization is detected optionally by means of a further binding partner for the nucleic acid of the sample and/or the nucleic acid probe.

The CTp11 nucleic acids are therefore valuable prognostic markers in the diagnosis of the metastatic and progression potential of tumor cells of a patient.

There is further provided a method for producing a protein whose expression is correlated with tumor metastasis, by expressing an exogenous DNA in prokaryotic or eukaryotic host cells and isolation of the desired protein, wherein the protein is coded by the nucleic acid molecules according to the invention, preferably by the DNA sequence shown in SEQ ID NO:1.

The protein can be isolated from the cells or the culture supernatant and purified by chromatographic means, preferably by ion exchange chromatography, affinity chromatography and/or reverse phase HPLC.

The invention further comprises an isolated protein which is encoded by a nucleic acid molecule according to the invention, preferably having the nucleotide sequence set forth in SEQ ID NO: 1.

CTp11 is especially characterized as a tumor progression gene, and as an upregulated gene indicative for metastatic potential of melanoma cells. The function of CTp11 is to promote loss of contact inhibition and anchorage dependence in tumor cells and to promote other essential steps of the metastatic cascade. Therefore the expression of CTp11 gene correlates with a more aggressive behavior of the tumor cells and also with the potential of the formation of metastasis.

According to the invention inhibitors for the expression of CTp11, preferably antisense nucleic acids or antibodies, can be used to inhibit tumor progression/metastasis, preferably of malignant melanomas and mammary carcinomas, in vivo, preferably by somatic gene therapy. Antibodies against CTp11 protein can be produced according to the state of the art using CTp11 protein purified as described above for immunization of mice or rats. Antisense nucleic acids preferably have a length of 20–100 nucleotides.

Overall characteristics place the gene in the family of cancer/testis antigens (CTAs) of which the first members, named MAGEs (melanoma antigens), were described by the group of Boon (van der Bruggen et al., Science 254 (1991) 1643–1647).

The protein encoded by the full-length cDNA consists of 97 amino acids containing a bipartite nuclear localization signal (NLS). A specific nuclear localization was found after fusing the ORF in front of eGFP, indicating that the bipartite-like nuclear localization sequence is indeed effective. The bipartite NLS consensus comprises two basic amino acids (lysine (K) or arginine (R)) separated by a region of ten amino acids from a basic cluster in which three out of the next five residues must be basic (Dingwall and Laskey, Trends. Biochem. Sci. 16 (1991) 478–481). The spacer of ten amino acids was shown to be optimal, though effective bipartite nuclear localization signals were also found with elongated spacers (Robbins, J., et al., Cell 64 (1991) 615–623). This indicates the likeliness of the bipartite sequence in CTp11 (a.a. 40–57), with a 12 residue spacer, being responsible for localization in the nucleus. Bipartite NLS sequences have also been found in several members of the SSX-family, which also belong to the group of cancer/testis antigens (Dos Santos, N. R., et al., Hum. Mol. Genet. 6 (1997) 1549–1558). The acidic C-terminal region with the high content of glutamic acid residues resembles a GAL4 domain, shown to be effective in transcriptional activation after interaction or fusion with a DNA binding protein or domain (Mitchell, P. J., and Tjian, R., Science 245 (1989) 371–378). CTp11, like the SSX proteins (Dos Santos, N. R., et al., Hum. Mol. Genet. 6 (1997) 1549–1558) and melanocyte-specific gene 1 (MSG1) (Shioda, T., et al., Proc. Natl. Acad. Sci. USA 93 (1996) 12298–12303), lacks a DNA-binding domain. Therefore, it interacts with the transcription-initiation complex in order to concert its putative transcriptional regulation. The high percentage of charged amino acids might contribute in such a protein-complex interaction.

The expression profile of CTp11 in normal tissues, tumor cell lines and tumor samples place the gene in the group of cancer/testis antigens, which already include MAGE (Lucas, S., et al., Cancer Res. 58 (1998) 743–752), BAGE (Boel, P., et al., Immunity 2 (1995) 167–175), GAGE (van den Eynde, B., et al., J. Exp. Med. 182 (1995) 689–698), SSX (Gure, A. O., et al., Int. J. Cancer 72 (1997) 965–971), NY-ESO-1 (Chen, Y. T., et al., Proc. Natl. Acad. Sci. USA 94 (1997) 1914–1918), LAGE-1 (Lethe, B., et al., Int. J. Cancer 76 (1998) 903–908), PAGE-1 (Chen, M. E., et al., J. Biol. Chem. 273 (1998) 17618–17625; Brinkmann, U., et al., Proc. Natl. Acad. Sci. USA 95 (1998) 10757–10762) and SCP-1 (Tureci, O., et al., Proc. Natl. Acad. Sci. USA 95 (1998) 5211–5216).

Criteria genes should fullfil to be considered as a member of the family of cancer/testis antigens are formulated in the literature (Chen, Y. T., et al., Proc. Natl. Acad. Sci. USA 94 (1997) 1914–1918; Chen, Y. T., et al., Proc. Natl. Acad. Sci. USA 95 (1998) 6919–6923): (i) predominant expression in testis and generally not in other normal tissues, (ii) induction/activation of mRNA expression in a wide range of human tumors, (iii) expression in malignancies in a lineage-nonspecific fashion, (iv) often existence of multigene families, (v) mapping of the gene, with some exceptions, on the X-chromosome. CTp11 clearly qualifies as a CTA-family member since it shares criteria i, ii, iii and v.

The CTp11 gene is localized on the X chromosome (Xq26.3-Xq27.1) and consist of two exons separated by an intron of about 655 bp as confirmed by PCR. This position is right next to the MAGE-C subfamily (Xq26) (Lucas, S., et al., Cancer Res. 58 (1998) 743–752) and nearby CTAG (the gene for NY-ESO-1) and the MAGE-A cluster (both Xq28) (Chen, Y. T., et al., Cell Genet. 79 (1997) 237–249).

CTp11 expression was found in 25–30% of the melanoma and bladder tumor cell lines tested, while cell lines established from other tumor types were only sporadically positive. For melanoma cell lines, which are the best studied regarding CTA expression, the percentage of positivity is comparable to the percentages of positivity for NY-ESO-1 (18%) (Chen, Y. T., et al., Proc. Natl. Acad. Sci. USA 94 (1997) 1914–1918; Lethe, B., et al., Int. J. Cancer 76 (1998) 903–908), SSX-2 (25%) (Tureci, O., et al., Int. J. Cancer 77 (1998) 19–23) and MAGE-B1 and -B2 (22% and 33%) (Lurquin, C., et al., Genomics 46 (1997) 397–408; Muscatelli, F., et al., Proc. Natl. Acad. Sci. USA 92 (1995) 4987–4991). MAGE-A1 (66%) (Kirkin, A. F., et al., Exp. Clin. Immunogenet. 15 (1998) 19–32; Wang, R. F., Mod. Med. 3 (1997) 716–731) has a markedly higher expression coverage in melanoma cell lines and is expressed in 41% of other human tumor cell lines.

Testis-specific expression regarding normal tissues seen by RT-PCR confirms the exclusiveness of CTp11 homology with only ESTs from testis. In fresh human tumor samples, melanoma was found to have the highest percentage of CTp11 positivity (70%; n=10). Comparable positivity was seen in primary (3 out of 4) as well as metastatic melanoma (4 out of 6). This percentage may be one of the highest compared to the other CTAs in melanoma, being 8, 17, 22, 35, 44, 44 and 52% for SCP-1, GAGE, BAGE, MAGE-1, SSX-2, NY-ESO-1 and MAGE-3 (Sahin, U., et al., Int. J. Cancer 78 (1998) 387–389), respectively. The relatively high percentage of CTp11 in bladder cell lines (30%) was not detected in bladder tumor samples in which only 1 out of 11 was found to be positive.

Interestingly, testis tumors showed a downregulation of CTp11 expression compared to normal testis tissue, since only 10 out of 17 tumor lesions were positive after nested PCR. No positivity of testis tumor samples was seen after the first PCR. Positivity of these testis lesions, both seminomas and non-seminomas, could be caused by small amounts of normal testis tissue present. Regarding the other CTAs it is known that MAGE-1 is mainly expressed in germ cells of the testis (Takahashi, K., et al., Cancer Res. 55 (1995) 3478–3482) and this finding is in line with the fact that seminoma have a higher positivity rate for MAGE-expression than non-seminoma tumors (Hara, I., et al., Urology 53 (1999) 843–847).

Homology Search and Chromosomal Localization

Checking all kinds of databases, there was found homology of more than 90% with three human genomic clones (HS433M19; HS376H23; HSG164F24), all localized on chromosome X. The homology with HS433M19 even narrowed the gene-localization down to Xq26.3-Xq27.1. PCR on a panel of human chromosome specific rodent/human hybrid cell lines confirmed localization of the gene on chromosome X. Based on the length of the genomic PCR product and on the sequences of the three human genomic clones it was deduced that the gene consists of two exons separated by an intron of approximately 655 bp which is located near basepair 112.

Homology on cDNA level was restricted to several human ESTs which were all from testis (zt95b09; qg57b01; qe04h11; EST95628/EST95629) and which all code for the same putative protein. Homology was also found with EMBL Database ACC No. AI962751, AA412605, and AA412270 as well as with SEQ ID NO:18 and SEQ ID NO:75 of WO 99/46374.

The invention further provides methods for identifying and isolation of antagonists of CTp11 or inhibitors for the expression of CTp11 (e.g. antisense nucleotides). Such antagonists or inhibitors can be used to inhibit tumor progression or metastasis and cause massive apoptosis of tumor cells in vivo.

According to the invention there are provided methods for identifying and isolation of compounds which have utility in the treatment of cancer, especially in inhibiting metastasis and related disorders. These methods include methods for modulating the expression of the polypeptides according to the invention, methods for identifying compounds which can selectively bind to the proteins according to the invention, and methods of identifying compounds which can modulate the activity of said polypeptides. The methods further include methods for modulating, preferably inhibiting, the transcription of CTp11 gene to mRNA, which preferably down-regulates the metastatic potential of a tumor cell. These methods can be conducted in vitro or in vivo and may make use of and establish cell lines and transgenic animal models of the invention.

A CTp11 antagonist is defined as a substance or compound which decreases or inhibits the biological activity of CTp11, a polypeptide and/or inhibits the transcription or translation of CTp11 gene. In general, screening procedures for CTp11 antagonists involve contacting candidate substances with host cells in which invasiveness is mediated by expression of CTp11 under conditions favorable for measuring CTp11 activity.

CTp11 activity may be measured in several ways. Typically, the activation is apparent by a change in cell physiology, such as increased mobility and invasiveness in vitro, or by a change in the differentiation state, or by a change in cell metabolism leading to an increase of proliferation.

The CTp11 gene and protein can be used to identify and design drugs which interfere with proliferation and dissemination of tumor cells.

The following examples, references, sequence listing and figures are provided to aid the understanding of the present invention. It is understood that modifications can be made in the procedures set forth without departing from the spirit of the invention.

SEQ ID NO:1: cDNA and amino acid sequence of CTp11.
SEQ ID NO:2: Amino acid of CTp11.
SEQ ID NO:3: Sense primer.
SEQ ID NO:4: Antisense primer.
SEQ ID NO:5: Nested sense primer.
SEQ ID NO:6: Nested antisense probe.
SEQ ID NO:7: β2-Microglobulin-sense primer.
SEQ ID NO:8 β2-Microglobulin antisense primer.

EXAMPLE 1

Materials and Methods

Cell Lines and Primary Cultures

A panel of eight different human melanoma cell lines containing 530, 1F6, MV1, M14, Mel57, BLM, MV3, and 1F6m was described earlier (Westphal, J. R., et al., Br. J. Cancer 76 (1997) 561–570; van Muijen, G. N., et al., Clin. Exp. Metastasis 9 (1991) 259–272). In this panel of cell lines 530 and 1F6 are poorly metastatic, while MV3, BLM and 1F6m are highly metastatic cell lines. MV1, M14, and Mel57 are cell lines with an intermediate metastatic capacity. 1F6m is a metastatic subline of 1F6. Most other cell lines used were described earlier (Zendman, A. J., et al., FEBS Lett. 446 (1999) 292–298). Cell lines RAMOS and RAJI are from the ATCC. BLM is an HLA-A1 negative melanoma cell line. All cell lines were grown in Dulbecco's modified Eagle's medium as described earlier (de Vries, T. J., et al., Cancer Res. 56 (1996) 1432–1439). Normal human foreskin melanocytes and human nevus cells were cultured as described previously (Verbeek, M. M., Am. J. Pathol. 144 (1994) 372–382).

Human Tissues

Lesions from all stages of melanocytic tumor progression (common nevi, atypical nevi, primary melanoma and melanoma metastases) and other tumor specimens were excised from patients at the University Hospital Nijmegen, The Netherlands. As normal human tissues, disease-free samples from surgically removed tissues or from autopsies with a post-mortem delay shorter than 4 hours were used. Tissue samples were snap-frozen in liquid nitrogen and stored at −80° C. until use.

RNA Isolation

From cultured cells total RNA was isolated using the RNeasy kit (Qiagen, Hilden, Germany) following the manufacturer's protocol. From tissue samples total RNA was isolated (following manufacturer's protocol) by disrupting about 25 frozen sections of 20 μm thickness in 1 ml RNAzolB™ (Campro, Veenendaal, The Netherlands) using a pestle. The RNAzolB™ method was followed by an additional RNeasy cleaning step.

mRNA Differential Display

Prior to mRNA differential display PCR, DNaseI treatment was performed on the RNA samples using the Message-Clean™ kit (GenHunter Corporation, Nashville, Tenn.). For differential display the RNAmap™ protocol (GenHunter) was used with some minor modifications.

Differing from the original protocol, [$^{32}$P]-dATP was used instead of [$^{35}$S]-dATP. For the PCR, combinations of the four $T_{12}$MN primers together with six arbitrary primers, AP$^{2, 6, 7, 11, 12}$ (Bauer, D., et al., NucleicAcids. Res. 21 (1993) 4272–4280), were used.

Northern Blotting

Ten micrograms of total RNA were treated with glyoxal/DMSO (Sambrook et al., Molecular Cloning: A Laboratory Manual (1989), Cold Spring Harbor Laboratory Press, New York, USA), separated on a 1.2% agarose gel and blotted onto a Hybond N$^+$ membrane (Amersham, Aylesbury, UK). cDNA probes were radiolabeled by [$^{32}$P]-dATP incorporation using a random-primed DNA labeling kit (Roche Diagnostics GmbH, Penzberg, Germany). Membranes were hybridized overnight with the radiolabeled probes at 65° C. in a hybridization mix (0.25 M sodium phosphate buffer pH 7.2, 7% SDS, 1% BSA, 1 mM EDTA, 0.1 mg/ml single stranded Salmon sperm DNA). Afterwards membranes were washed at 65° C. with buffers containing decreasing amounts of salt (1% SDS, 1 mM EDTA and 125 mmol/l sodium phosphate pH 7.2), and autoradiographed using Kodak Xomat-S films.

cDNA Library Screening, Sequencing and Homology Searching cDNA probes were labeled as described in Sambrook et al., Molecular Cloning: A Laboratory Manual (1989), Cold Spring Harbor Laboratory Press, New York, USA and hybridized to a λZAP cDNA library of a human melanoma cell line (MV3). After isolation of a full-length cDNA, both strands were sequenced using the Dye Terminator Reaction Mix (Perkin Elmer, Norwalk, Conn.). Homology searches were performed with BLAST (Altschul, S. F., et al., Nucleic Acids Res. 25 (1997) 3389–3402) and other software on all kinds of public servers of DNA and protein databases as described earlier (Zendman, A. J., et al., FEBS Lett. 446 (1999) 292–298).

RT-PCR

Synthesis of cDNA (10' at 25° C., followed by 59' at 42° C.) was performed on 0.5–1.0 µg of total RNA using the AMV RT kit (Roche Diagnostics GmbH). The reaction mixture was supplemented with 0.04 U of random hexadeoxynucleotide primers, 2 µl 25 mM MgCl$_2$, 1 µl 10 mM dNTPs, 1 µl of RT buffer (100 mM Tris/HCl pH 8.3, 500 µM KCl), 25 U RNasin, 10 U AMV RT and water to a final volume of 10 µl. For amplification one tenth of the cDNA was supplemented with 2.5 µl PCR-buffer (200 mM (NH$_4$)$_2$SO$_4$, 750 mM Tris/HCl pH 9, 0.1% Tween), 5 µl 1M dNTPs, 10 pmoles of each primer, 2.5 µl 15 mM MgCl$_2$, 0.15 U of Thermoperfectplus™ DNA polymerase (Integro, Zaandam, The Netherlands) and water to a final volume of 25 µl. PCR conditions were 45" at 94° C., 1' at 59° C. and 1'30" at 72° C. for 30 cycles. These cycles were preceded by 3 min. denaturation at 94° C. and followed by a 5 min. elongation step at 72° C. The primer combination used was:

sense: 5'-CTGCCGCAGACATTGAAGAA-3' (SEQ ID NO:3)

antisense: 5'-TCCATGAATTCCTCCTCCTC-3' (SEQ ID NO:4)

The PCR product length was 297 bp. When nested PCR was performed the conditions were 30" at 94° C., 45" at 59° C. and 1' at 72° C. for 30 cycles, again preceded by denaturation and followed by elongation steps as described for the first PCR. For this nested PCR there were used 2 µl of 100 times diluted product from the first PCR, again in a total volume of 25 µl. Nested primers used were:

sense: 5'-TGTGAATCCAACGAGGTGAA-3' (SEQ ID NO:5)

antisense: 5'-TTGATTCTGTTCTCTCGGGC-3' (SEQ ID NO:6)

Nested PCR product length was 188 bp.

β2-Microglobulin primers used were:

sense: 5'-CTCGCGCTACTCTCTCTTTCT-3' (SEQ ID NO:7)

antisense: 5'-TGTCGGATTGATGAAACCCAG-3' (SEQ ID NO:8)

The β$_2$-microglobulin PCR product length was 136 bp. DNA molecular weight markers were from Roche Diagnostics GmbH.

Chromosomal Localization

Chromosomal localization of the gene was determined by genomic PCR on a panel of hamster/human and mouse/human hybrid cell lines (Kondoh, M., et al., Melanoma Res. 3 (1993) 241–245). For this PCR the intron enclosing primers of the first PCR shown above were used, yielding a 1 kb PCR product.

Plasmid Construction and Transfection

For localization studies a fragment (bp 1-330) was cloned, containing the full length ORF minus the termination codon, in the SacI-KpnI sites of pEGFP-N3 (Clontech, Palo Alto, Calif.). This fuses eGFP C-terminally to the fragment with a linker coding for amino acids RSIAT. The in-frame junction was confirmed by sequencing. Transfections were performed using FuGENE™6 transfection reagent (Roche Diagnostics GmbH). In short, BLM cells were seeded in 6 well plates and grown till subconfluency. Transfections were performed with 1 µg plasmid construct and 3 µl FuGENE™6 in 2 ml medium. Transient expression of the fusion protein was checked within 48 hours. Stable transfectants were created under Geneticin (Roche Diagnostics GmbH) selection (500 µg/µl).

To visualize expression of the fusion protein, cells (grown on coverslips in 6 well plates) were fixed with 4% paraformaldehyde for 15 minutes at room temperature and subsequently placed for 2 minutes in acetone at −20° C. Air-dried coverslips were put on a glass slide and mounted with 10 µl Tris-buffered glycerol (per 100 ml: 90 ml glycerol; 2 ml Tris/HCl pH 8; 8 ml H$_2$O) containing 1:4 Vectashield (Vector, Burlingame, Calif.) and 1:10.000 DAPI (Sigma, Zwijndrecht, The Netherlands). Fluorescent images were obtained using a fluorescence microscope equipped with a CCD camera.

Western Blotting

Cultured cells were lysed in SDS-lysis buffer (1% SDS; 5 mM EDTA; 10 µg/ml leupeptin (Sigma); 200 µg/ml AEBSF (Sigma) and 10 µg/ml chymostatin (Sigma) in PBS). After centrifugation equal protein amounts of supernatant were diluted 1:1 with non-reducing sample buffer and boiled for 5 minutes. These samples were size-separated using SDS PAGE on a 10% gel along with a protein marker and afterwards blotted electrophoretically on a nitrocellulose membrane in blotting buffer (25 mM Tris/HCl pH 8.6; 192 mM glycin; 20% methanol and 0.02% SDS). The marker-lane was separated and stained with amidoblack (0.1% amidoblack in methanol:acetic acid:water of 45:10:45) for size-reference. Previous to incubations blots were washed for 15 minutes in PBST and overnight incubated at room temperature with blocking solution (PBST containing 5% low fat milk powder and 0.01% antifoam A (Sigma)). The blot was incubated for 1 hour with anti-eGFP polyclonal rabbit antiserum as first antibody and with peroxidase-labeled swine-anti-rabbit antiserum (Dako, Glostrup, Denmark) as second antibody. All incubations were performed in blocking solution and after each step the blot was washed 3 times 10 minutes in PBST. Detection was done with ECL chemoluminescence (Roche Diagnostics GmbH) according to manufacturer's protocol. Blots were then exposed to Kodak Xomat-S films and developed.

EXAMPLE 2

Isolation and Cloning of CTp11

Comparing mRNA expression between human melanoma cell lines 1F6 and 1F6m with differential display, using primer $T_{12}MA$ in combination with $AP_1$ (Bauer, D., et al., Nucleic Acids. Res. 21 (1993) 4272–4280), yielded a 300 bp differential cDNA band. The band was abundantly present in the 1F6m lane and absent in the 1F6 lane. To study the expression in a broader panel of human melanoma cell lines with known metastatic behavior after subcutaneous inoculation into nude mice, Northern blotting was performed, using the 300 bp cDNA as a probe. This revealed a mRNA of about 0.5 kb that was specifically expressed in the highly metastatic cell lines MV3, BLM and 1F6m (FIG. 1). No expression could be detected in the intermediate and low metastatic cell lines.

To isolate a full length cDNA clone, a λZAP cDNA library of the MV3 melanoma cell line was screened, using the 300 bp cDNA fragment as a probe. A 408 bp cDNA was picked up (EMBL: AJ238277). Sequencing revealed a perfect 3' match with the probe used and showed an ORF coding for a protein of 97 amino acids (FIG. 2). This putative protein contains a possible bipartite nuclear localization signal (NLS) (a.a. 40–57), though it is not completely consensus (Dingwall and Laskey, Trends. Biochem. Sci. 16 (1991) 478–481). Another remarkable feature is its high content of glutamic acid residues (14%) resulting in an acidic C-terminal cluster (a.a. 83–89). Overall one third of the residues are charged (18 negative; 14 positive) and the expected molecular weight is 11 kD. The protein has a calculated pI of 5.0.

EXAMPLE 3

Expression Profile of CTp11

In addition to Northern blotting of the panel of human melanoma cell lines with known metastatic behavior, RT-PCR on RNA of these cell lines was also performed. The PCR results confirmed the expression pattern of the melanoma cell lines seen on Northern blots (Table 1).

TABLE 1 mRNA expression determined by RT-PCR in cultured human melanoma cell lines and in subcutaneous xenograft lesions

| Cell line | Metastatic potential | Cultured cells | Xenografts[a] |
|---|---|---|---|
| 530 | low | − | − |
| 1F6 | low | − | NT |
| MV1 | intermediate | − | − |
| M14 | intermediate | − | NT |
| Mel57 | intermediate | − | − |
| 1F6m | high | + | + |
| MV3 | high | + | + |
| BLM | high | + | + |

[a]NT: not tested

A specific product could only be detected in the highly metastatic cell lines 1F6m, MV3 and BLM. RT-PCR analysis on corresponding xenograft material also showed an expression profile that completely matched with the expression profile of the cultured cell lines. Analysis of a larger series of human melanoma cell lines not studied in the nude mouse model showed expression in 3 (BRO, E10 and 518A2) out of 15 cell lines (Table 2).

TABLE 2 mRNA expression determined by RT-PCR in human tumor cell lines

| Type of tumor cell line | Expression |
|---|---|
| kidney | 0/6 |
| prostate | 0/7 |
| bladder | 5/17 |
| melanoma | 6/23[a] |
| other | 2/16 |

[a]melanoma cell lines listed in Table 1 are included.

Regarding expression in cell lines derived from other types of malignant tumors (Table 2), expression was found in 5 out of 17 bladder carcinoma cell lines whereas 6 kidney carcinoma cell lines and 7 prostate carcinoma cell lines did not express the gene. Finally, of 16 cell lines from other histological type than the ones already mentioned only two were positive (fibrosarcoma HT1080 and osteosarcoma U20S).

Figure 3:
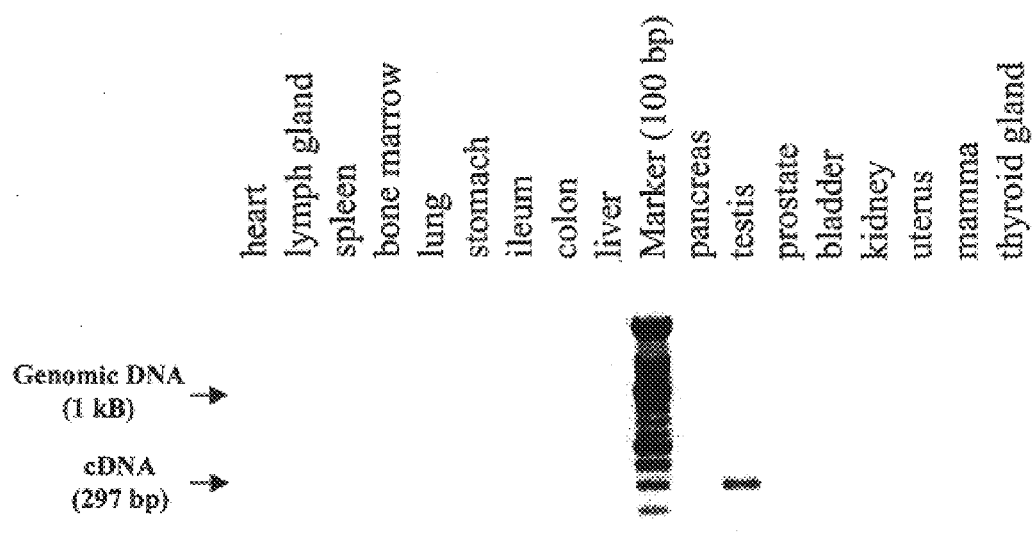
FIG. 3 (A) RT-PCR on RNA isolated from 17 different fresh normal human tissues. Only testis is positive (297 bp cDNA band). In a few samples a weak genomic DNA band is visible (1 kb). (B) Control RT-PCR of $\square_2$-microglobulin (136 bp).

Expression of the gene in normal human tissues determined by RT-PCR is shown in FIG. 3. From 17 different tissue samples tested only testis was found to be positive.

Figure 4:
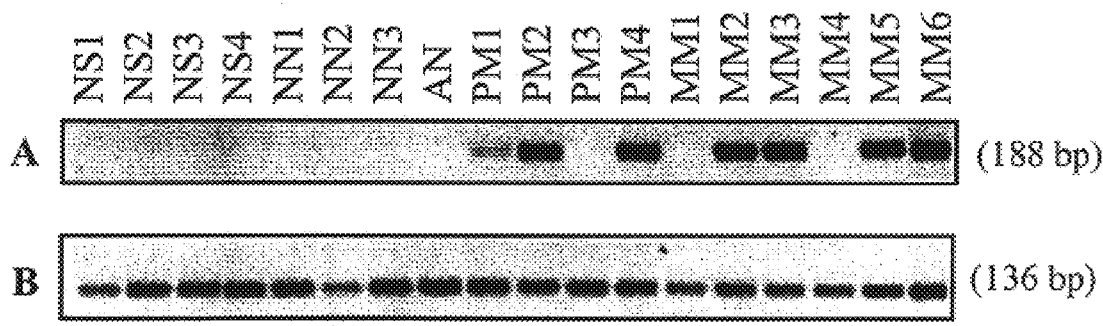
FIG. 4 (A) Nested RT-PCR (188 bp) on RNA isolated from samples of normal human skin and on RNA isolated from tissue samples containing lesions with different stages of melanocytic tumor progression (NS=normal skin; NN=common naevus naevocellularis; AN=atypical naevus; PM=primary melanoma; MM=melanoma metastasis). (B) Control RT-PCR of $\beta_2$-microglobulin.

A series of melanocytic lesions covering all stages of tumor progression for presence of the gene transcript was screened (FIG. 4). Nested RT-PCR analysis showed that PCR product was only detectable in advanced stages of melanocytic tumor progression. Three out of 4 primary melanomas (PM) and 4 out of 6 melanoma metastases (MM) were positive. No expression was found in normal skin (NS), common naevus naevocellularis (NN) and atypical nevus (AN). Primary cultures of normal human foreskin melanocytes and cultures of naevus cells were also negative.

Expression was also determined in additional samples of fresh normal human tissues and in tumor lesions from the same types of tissue. The results are summarized in Table 3.

TABLE 3 mRNA expression determined by nested RT-PCR in normal human tissues and in different types of cancer

| Tissue type | Normal tissue | Tumor tissue |
|---|---|---|
| pancreas | 0/3 | 0/5 |
| esophagus | 0/3 | 0/6 |
| lung | 0/3 | 1/5 |
| breast | 0/1 | 1/4 |
| colon | 0/3 | 2/9 |
| bladder | 0/1 | 1/11 |
| melanoma | 0/4[a] | 7/10 |
| testis | 3/3 | 10/17[b] |

[a]normal skin;
[b]positivity may be caused by contaminating normal tissue

Using nested PCR in the normal tissues expression was only seen in the three testis samples, which were already positive after the first PCR (30 cycles). The other normal tissues did not reveal any PCR product. In the tumor samples only sporadically expression was seen: lung (1 out of 5), breast (1 out of 4), colon (2 out of 9) and bladder (1 out of 11). Pancreas (n=5) and esophagus (n=6) tumors were negative. Regarding the testis lesions studied 10 out of the 17 tumor samples were positive, only after nested PCR, while three normal testis samples were positive already after the first round of PCR.

EXAMPLE 4

Molecular Weight Determination and Cellular Localization of CTp11

To determine the molecular weight of the protein, Western blotting was performed on lysates from the BLM transfectant using an anti-eGFP polyclonal antibody to detect the fusion protein. The transfected cells expressed the fusion protein. No specific band was seen in the lane containing lysate of non-transfected BLM cells. From the difference in size of eGFP (27 kD) and the fusion protein (38 kD) the size of the protein was deduced to be about 11 kD. Based on the mRNA expression profile and the molecular weight, the protein was named CTp11 : cancer/testis-associated protein of 11 kD.

To get insight into the subcellular localization of CTp11 the complete ORF was fused in front of eGFP and transfected COS-1 cells. As a control, COS-1 cells were transfected with a construct coding for eGFP alone. Fluorescence microscopy of COS-1 cells transfected with eGFP alone revealed the eGFP protein to be present both in the cytoplasm and in the nucleus as expected whereas COS-1 cells expressing the fusion protein showed specific nuclear localization of the product; nucleoli appear negative for the fusion protein. Transfection of the human melanoma cell line BLM showed comparable results with identical nuclear localization.

EXAMPLE 5

Procedure for Identification of Modulators of the Activity of the Protein According to the Invention The expression vector of Example 1 is transferred into NIH 3T3 cells by standard methods known in the art (Sambrook et al.). Cells which have taken up the vector are identified by their ability to grow in the presence of the selection or under geneticin selective conditions. Cells which express DNA encoding CTp11 produce RNA which is detected by Northern blot analysis as described in Example 1. Alternatively, cells expressing the protein are identified by identification of the protein by Western blot analysis using specific antibodies. Cells which express the protein from the expression vector will display metastatic potential measured according to Example 3.

Cells which express the protein are cultured with and without a putative modulator compound. By screening of chemical and natural libraries, such compounds can be identified using high throughput cellular assays monitoring cell growth (cell proliferation assays using as chromogenic substrates the tetrazolium salts WST-1, MTT, or XTT, or a cell death detection ELISA using bromodesoxyuridine (BrdU); cf. Boehringer Mannheim GmbH, Apoptosis and Cell Proliferation, $2^{nd}$ edition, 1998, pp. 70–84).

The modulator compound will cause a decrease in the cellular response to the CTp11 protein activity and will be an inhibitor of CTp11 function.

Alternatively, putative inhibitors are added to cultures of tumor cells, and the cells display reduced altered metastatic properties. A putative modulator compound is added to the cells with and without CTp11 protein and a cellular response is monitored by growth properties of the cell.

EXAMPLE 6

Antibodies Against CTp11

Recombinantly produced CTp11 polypeptide is coupled to BSA. Rabbits are interdermally immunized separately with these immunogens in a first immunization (500 μg immunogen, Freund's adjuvant) and with further intravenous boosts (500 μg immunogen, Freund's adjuvant). Test bleeds were done one week after each boost and binding was tested against the antigen of the immunogens and the full length CTp11 protein.

List of References

Albelda, S. M., Lab. Invest. 68 (1993) 4–17
Altschul, S. F., et al., Nucleic Acids Res. 25 (1997) 3389–3402
Ausubel I., Frederick M., Current Protocols in Mol. Biol. (1992), John Wiley and Sons, New York
Bauer, D., et al., Nucleic Acids. Res. 21 (1993) 4272–4280
Boel, P., et al., Immunity 2 (1995) 167–175
Boehringer Mannheim GmbH, Apoptosis and Cell Proliferation, $2^{nd}$ edition, 1998, pp. 70–84
Brinkmann, U., et al., Proc. Natl. Acad. Sci. USA 95 (1998) 10757–10762
Büttner et al., Mol. Cell. Biol. 11 (1991) 3573–3583
Chen, M. E., et al., J. Biol. Chem. 273 (1998) 17618–17625
Chen, Y. T., et al., Cell Genet. 79 (1997) 237–249
Chen, Y. T., et al., Proc. Natl. Acad. Sci. USA 94 (1997) 1914–1918
Chen, Y. T., et al., Proc. Natl. Acad. Sci. USA 95 (1998) 6919–6923
de Vries, T. J., et al., Cancer Res. 56 (1996) 1432–1439
Dingwall and Laskey, Trends. Biochem. Sci. 16 (1991) 478–481
Dos Santos, N. R., et al., Hum. Mol. Genet. 6 (1997) 1549–1558
Ebnet, K., et al., Annu. Rev. Immunol. 14 (1996) 155–177
EMBL Database AI962751
EMBL Database AA412605
EMBL Database AA412270
EP-A 0 063 879
EP-A 0 128 018
EP-A 0 173 251
EP-A 0 200 362
Gure, A. O., et al., Int. J. Cancer 72 (1997) 965–971
Hames, B. D., Higgins, S. G., Nucleic Acid Hybridisation—A Practical Approach (1985) IRL Press, Oxford, England
Hara, I., et al., Urology 53 (1999) 843–847
Kirkin, A. F., et al., Exp. Clin. Immunogenet. 15 (1998) 19–32
Kondoh, M., et al., Melanoma Res. 3 (1993) 241–245
Lethe, B., et al., Int. J. Cancer 76 (1998) 903–908
Lucas, S., et al., Cancer Res. 58 (1998) 743–752
Lurquin, C., et al., Genomics 46 (1997) 397–408
Mitchell, P. J., and Tjian, R., Science 245 (1989) 371–378
Muscatelli, F., et al., Proc. Natl. Acad. Sci. USA 92 (1995) 4987–4991
Pardee, A. B., Advances in Cancer Res. 65 (1994) 213–227
Robbins, J., et al., Cell 64 (1991) 615–623
Sahin, U., et al., Int. J. Cancer 78 (1998) 387–389
Sambrook et al., Molecular Cloning: A Laboratory Manual (1989) Cold Spring Harbor Laboratory Press, New York, USA
Shioda, T., et al., Proc. Natl. Acad. Sci. USA 93 (1996) 12298–12303
Takahashi, K., et al., Cancer Res. 55 (1995) 3478–3482
Tureci, O., et al., Int. J. Cancer 77 (1998) 19–23
Tureci, O., et al., Proc. Natl. Acad. Sci. USA 95 (1998) 5211–5216
U.S. Pat. No. 2,915,082
van den Eynde, B., et al., J. Exp. Med. 182 (1995) 689–698
van der Bruggen et al., Science 254 (1991) 1643–1647
Van Groningen, J. M., et al., Cancer Res. 55 (1995) 6237–6243
van Muijen, G. N. P., et al., Clin. Exp. Metastasis 9 (1991) 259–272 van Muijen, G. N. P., et al., Int. J. Cancer 48 (1991) 85–91
Varner, J. A., and Cheresh, D. A., Curr. Opin. Cell Biol. 8 (1996) 724–730
Verbeek, M. M., Am. J. Pathol. 144 (1994) 372–382
Wahl, G. M., et al., Proc. Natl. Acad. Sci. USA 76 (1979) 3683–3687
Wang, R. F., Mod. Med. 3 (1997) 716–731
Westphal, J. R., et al., Br. J. Cancer 76 (1997) 561–570
Weterman, M. A. J., et al., Cancer Res. 52 (1992) 1291–1296
Weterman, M. A. J., et al., Int. J. Cancer 53 (1993) 278–284
Weterman, M. A. J., et al., Int. J. Cancer 60 (1995) 73–81
WO 89/06698
WO 99/46374
Zendman, A. J., et al., FEBS Lett. 446 (1999) 292–298

What is claimed is:

1. A process for detecting in a patient sample the presence or absence of at least one specific nucleic acid or mixture of nucleic acids, or distinguishing between two different sequences in said sample, wherein the sample is suspected of containing said sequence or sequences, which process comprises:

(a) incubating said sample under stringent hybridization conditions with a nucleic acid probe which is selected from the group consisting of:
(i) a nucleic acid sequence taken from the group consisting of SEQ ID NOS:1 and 3 to 6;
(ii) a nucleic acid sequence which is exactly complementary to any nucleic acid sequence of (i);
(iii) a nucleic acid sequence which hybridizes under stringent conditions with the sequence of (i); and
(iv) a nucleic acid sequence which hybridizes under stringent conditions with the sequence of (ii); and (b) determining whether said hybridization has occurred.

2. The process in accordance with claim 1, wherein said nucleic acid probe is bound to a carrier.

3. The process in accordance with claim 2, wherein the steps further comprise after step (a) and prior to step (b):

washing the resultant of step (a);

incubating the resultant of the wash step with a labeled antibody against the nucleic acid probe; and washing the resultant of the incubating step.

4. The process in accordance with claim 3, wherein step (b) further comprises determining whether any antibody conjugates are present.

5. An isolated nucleic acid which inhibits a nucleic acid in inducing tumor progression and metastasis, said isolated nucleic acid having a sequence selected from the group consisting of:

(a) a nucleic acid sequence which is exactly complementary to SEQ ID NO: 1; and
(b) a nucleic acid sequence which hybridizes under stringent conditions with the complementary sequence of (a).

6. A process for determining whether or not a tumor containing test sample has potential for tumor progression or metastasis, which process comprises:

(a) obtaining the test sample and a second sample free from metastasis wherein the test sample and the second sample are obtained from the same individual or different individuals of the same species;

(b) incubating each respective sample under stringent hybridization conditions with a nucleic acid probe which is selected from the group consisting of:
(i) a nucleic acid sequence taken from the group consisting of SEQ ID NOS:1 and 3 to 6;
(ii) a nucleic acid sequence which is exactly complementary to any nucleic acid sequence of (i);
(iii) a nucleic acid sequence which hybridizes under stringent conditions with the sequence of (i); and
(iv) a nucleic acid sequence which hybridizes under stringent conditions with the sequence of (ii); and (c) determining the approximate amount of hybridization of each respective sample with said probe, and (d) comparing the approximate amount of hybridization of the test sample to an approximate amount of hybridization of the sample which is free from metastasis, to identify whether or not the test sample contains a greater amount of the specific nucleic acid or mixture of nucleic acids than does the sample which is free from metastasis.

* * * * *

UNITED STATES PATENT AND TRADEMARK OFFICE
CERTIFICATE OF CORRECTION

PATENT NO. : 6,677,118 B1
DATED : January 13, 2004
INVENTOR(S) : Goos van Muijen and Albert Zendman It is certified that error appears in the above-identified patent and that said Letters Patent is hereby corrected as shown below:

Title page, Item [54] and Column 1, lines 1-4,
Title reads as follows: "PROCESS FOR THE DETERMINATION OF CTP11 AND FOR DETERMINING WHETHER A TUMOR SAMPLE HAS METASTATIC POTENTIAL". The Title should read as follows -- PROCESS FOR THE DETERMINATION OF $CT_p11$ AND FOR DETERMINING WHETHER A TUMOR SAMPLE HAS METASTATIC POTENTIAL --.

Title page,
Item [73], Assignee, reads "Hoffman-La Roche Inc., Nutley, NJ (US)." it should read -- Hoffmann-La Roche Inc., Nutley, NJ (US) --.

Signed and Sealed this

Fourth Day of May, 2004

JON W. DUDAS
*Acting Director of the United States Patent and Trademark Office*

SEQUENCE LISTING

```
<160> NUMBER OF SEQ ID NOS:   8

<210> SEQ ID NO 1
<211> LENGTH: 408
<212> TYPE: DNA
<213> ORGANISM: Homo sapiens
<220> FEATURE:
<221> NAME/KEY: CDS
<222> LOCATION: (40)..(333)

<400> SEQUENCE: 1
caaaagcctg ccgcagacat tgaagaacca atatataca atg gac aaa caa tcc         54
                                           Met Asp Lys Gln Ser
                                             1               5 agt gcc ggc ggg gtg aag agg agc gtc ccc tgt gaa tcc aac gag gtg       102
Ser Ala Gly Gly Val Lys Arg Ser Val Pro Cys Glu Ser Asn Glu Val
             10                  15                  20 aat gag acg atg ccg gag acc cca act ggg gac tca gac ccg caa cct       150
Asn Glu Thr Met Pro Glu Thr Pro Thr Gly Asp Ser Asp Pro Gln Pro
         25                  30                  35 gct cct aaa aaa atg aaa aca tct gag tcc tcg acc ata cta gtg gtt       198
Ala Pro Lys Lys Met Lys Thr Ser Glu Ser Ser Thr Ile Leu Val Val
     40                  45                  50 cgc tac agg agg aac gtg aaa aga aca tct cca gag gaa ctg ctg aat       246
Arg Tyr Arg Arg Asn Val Lys Arg Thr Ser Pro Glu Glu Leu Leu Asn
 55                  60                  65 gac cac gcc cga gag aac aga atc aac ccc ctc caa atg gag gag gag       294
Asp His Ala Arg Glu Asn Arg Ile Asn Pro Leu Gln Met Glu Glu Glu
70                  75                  80                  85 gaa ttc atg gaa ata atg gtt gaa ata cct gca aag tag caagaagcta       343
Glu Phe Met Glu Ile Met Val Glu Ile Pro Ala Lys
                 90                  95 catctctcaa ccttgggcaa tgaaataaa gtttgagaag ctgaaaaaaa aaaaaaaaa       403 aaaaa                                                                 408

<210> SEQ ID NO 2
<211> LENGTH: 97
<212> TYPE: PRT
<213> ORGANISM: Homo sapiens

<400> SEQUENCE: 2

Met Asp Lys Gln Ser Ser Ala Gly Gly Val Lys Arg Ser Val Pro Cys
 1               5                  10                  15

Glu Ser Asn Glu Val Asn Glu Thr Met Pro Glu Thr Pro Thr Gly Asp
                 20                  25                  30

Ser Asp Pro Gln Pro Ala Pro Lys Lys Met Lys Thr Ser Glu Ser Ser
             35                  40                  45

Thr Ile Leu Val Val Arg Tyr Arg Arg Asn Val Lys Arg Thr Ser Pro
         50                  55                  60

Glu Glu Leu Leu Asn Asp His Ala Arg Glu Asn Arg Ile Asn Pro Leu
 65                  70                  75                  80
```

```
Gln Met Glu Glu Glu Glu Phe Met Glu Ile Met Val Glu Ile Pro Ala
            85                  90                  95
Lys

<210> SEQ ID NO 3
<211> LENGTH: 20
<212> TYPE: DNA
<213> ORGANISM: Artificial
<220> FEATURE:
<223> OTHER INFORMATION: Sense Primer

<400> SEQUENCE: 3
ctgccgcaga cattgaagaa                                              20

<210> SEQ ID NO 4
<211> LENGTH: 20
<212> TYPE: DNA
<213> ORGANISM: Artificial
<220> FEATURE:
<223> OTHER INFORMATION: Antisense primer

<400> SEQUENCE: 4
tccatgaatt cctcctcctc                                              20

<210> SEQ ID NO 5
<211> LENGTH: 20
<212> TYPE: DNA
<213> ORGANISM: Artificial
<220> FEATURE:
<223> OTHER INFORMATION: Nested sense primer

<400> SEQUENCE: 5
tgtgaatcca acgaggtgaa                                              20

<210> SEQ ID NO 6
<211> LENGTH: 20
<212> TYPE: DNA
<213> ORGANISM: Artificial
<220> FEATURE:
<223> OTHER INFORMATION: Nested antisense primer

<400> SEQUENCE: 6
ttgattctgt tctctcgggc                                              20

<210> SEQ ID NO 7
<211> LENGTH: 21
<212> TYPE: DNA
<213> ORGANISM: Artificial
<220> FEATURE:
<223> OTHER INFORMATION: Beta2-Microglobulin-sense primer

<400> SEQUENCE: 7
ctcgcgctac tctctctttc t                                            21

<210> SEQ ID NO 8
<211> LENGTH: 21
<212> TYPE: DNA
<213> ORGANISM: Artificial
<220> FEATURE:
<223> OTHER INFORMATION: Beta2-Microglobulin-antisense primer

<400> SEQUENCE: 8
tgtcggattg atgaaaccca g                                            21
```